United States Patent
Edwin et al.

(10) Patent No.: US 7,449,881 B2
(45) Date of Patent: Nov. 11, 2008

(54) METHOD AND APPARATUS FOR DETERMINING THE THICKNESS OF A CHROMIUM DEPLETED ZONE OF A SURFACE REGION OF A STEEL MEMBER

(75) Inventors: Emil Edwin, Trondheim (NO); Tore Arnesen, Ranheim (NO)

(73) Assignee: Borealis Technology Oy, Porvoo (FI)

( * ) Notice: Subject to any disclaimer, the term of this patent is extended or adjusted under 35 U.S.C. 154(b) by 178 days.

(21) Appl. No.: 10/521,820

(22) PCT Filed: Jul. 22, 2003

(86) PCT No.: PCT/EP03/07997

§ 371 (c)(1),
(2), (4) Date: May 23, 2005

(87) PCT Pub. No.: WO2004/023133

PCT Pub. Date: Mar. 18, 2004

(65) Prior Publication Data
US 2005/0200354 A1    Sep. 15, 2005

(30) Foreign Application Priority Data
Jul. 22, 2002    (GB)    ................. 0216981.1

(51) Int. Cl.
G01B 7/06    (2006.01)
(52) U.S. Cl. .................... 324/229; 324/235
(58) Field of Classification Search .......... 324/228–243
See application file for complete search history.

(56) References Cited

U.S. PATENT DOCUMENTS 3,359,495 A * 12/1967 McMaster et al. .......... 324/235
3,440,527 A * 4/1969 Steingroever ............... 324/230
3,689,828 A    9/1972 Kurose et al.
3,761,804 A * 9/1973 Steingroever ............... 324/230
4,931,730 A    6/1990 Olsen et al.

(Continued)

FOREIGN PATENT DOCUMENTS

DE    19543362    11/1995

(Continued)

OTHER PUBLICATIONS

Takashi et al., Study of chromium depletion by magnetic method in Ni-based alloys, Feb. 2004, Journal of Magnetism and Magnetic material, vol. 269, Issue 2, pp. 139-149.*

Primary Examiner—Jay M Patidar
(74) Attorney, Agent, or Firm—Ballard Spahr Andrews & Ingersoll, LLP

(57) ABSTRACT

The invention provides a method and apparatus for monitoring subsurface chromium depletion from a steel member, such as a pyrolysis pipe. In the harsh conditions of a pyrolysis furnace, chromium within the pipe 16 migrates towards the pipe surface which results in the formation of a chromium depleted layer 14. This layer can provide useful data about the condition and operation of the furnace. The degree of chromium depletion is measured by using a magnetic source of known strength to create a magnetic field in the surface region of the pipe 16. An estimate of the thickness of the chromium depleted layer 14 is determined from the resultant magnetic flux, which can be measured by a hall element arranged at substantially 45° to the longitudinal axis of the magnet.

17 Claims, 6 Drawing Sheets

U.S. PATENT DOCUMENTS

| | | | |
|---|---|---|---|
| 5,105,151 A * | 4/1992 | Takahashi et al. | 324/235 |
| 5,128,613 A | 7/1992 | Takashi | |
| 5,343,146 A | 8/1994 | Koch | 324/230 |
| 5,828,212 A * | 10/1998 | Nix | 324/230 |
| 6,051,972 A | 4/2000 | Bour et al. | |

FOREIGN PATENT DOCUMENTS

| | | | |
|---|---|---|---|
| EP | 0028487 | * | 5/1981 |
| GB | 2271641 | | 9/1993 |
| GB | 2306006 | | 9/1996 |
| NO | 302202 | | 5/1996 |
| SU | 1375942 | | 2/1986 |

* cited by examiner

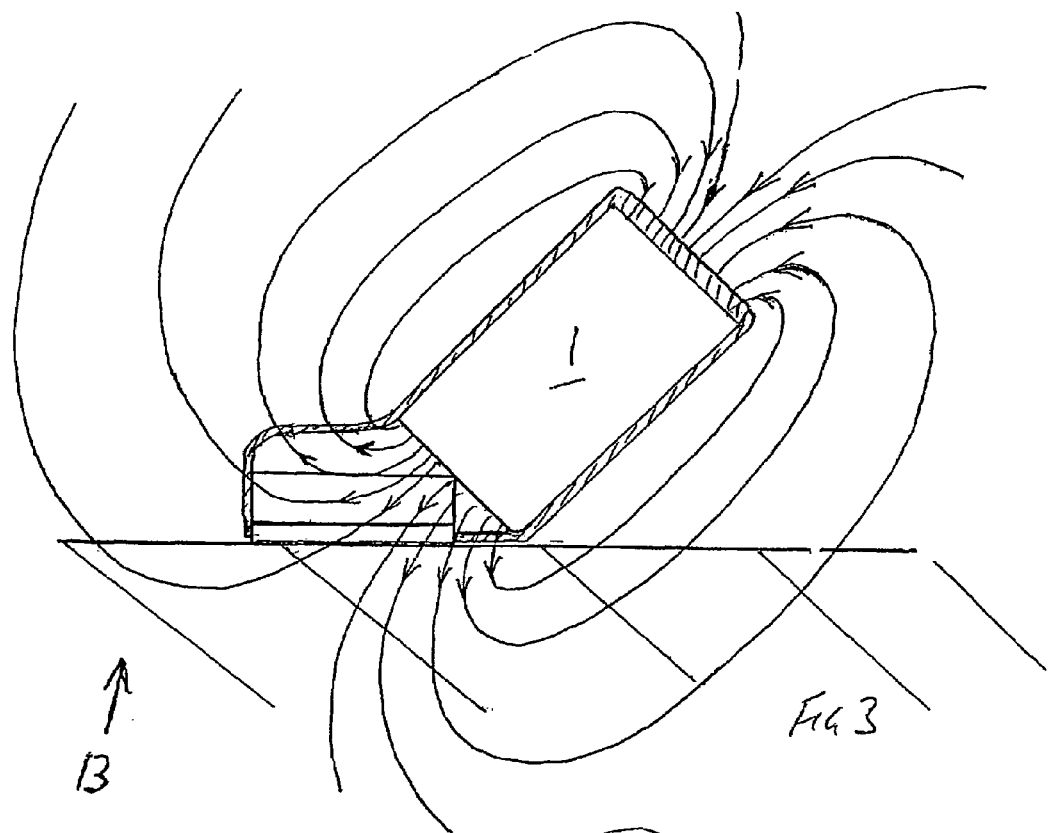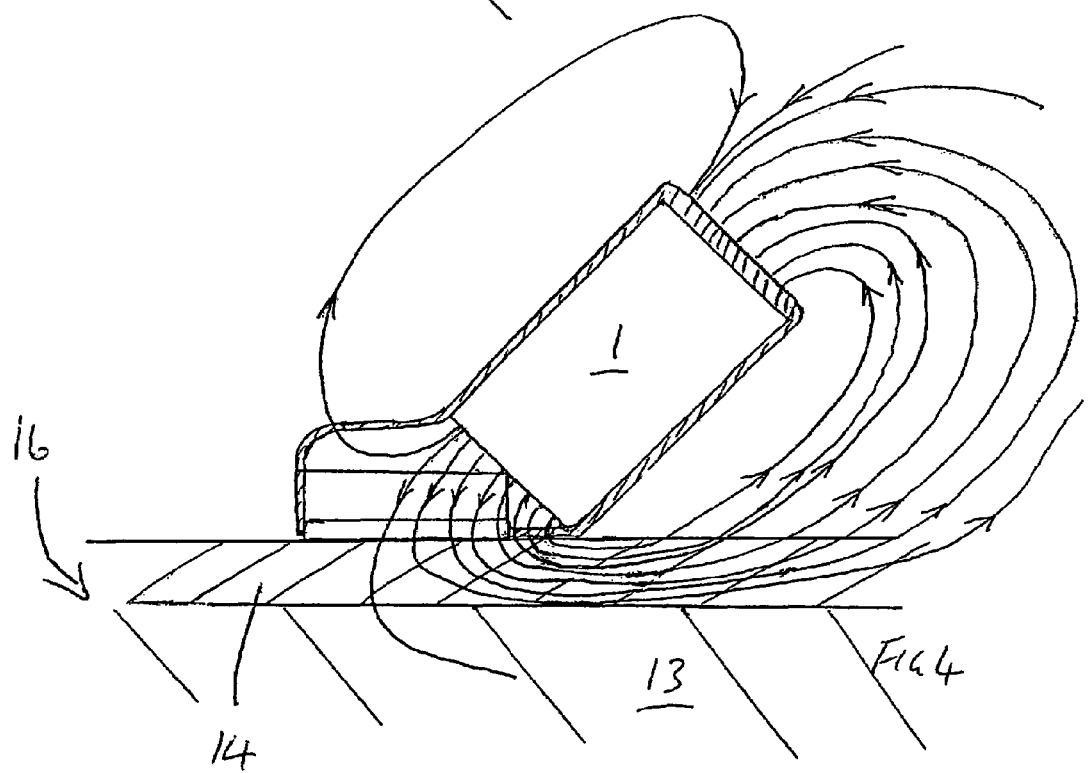

METHOD AND APPARATUS FOR DETERMINING THE THICKNESS OF A CHROMIUM DEPLETED ZONE OF A SURFACE REGION OF A STEEL MEMBER

CROSS REFERENCE TO RELATED APPLICATIONS

The present application claims priority to Great Britain Patent Application No. 0216981.1, filed Jul. 22, 2002 which application is incorporated herein fully by this reference.

The present invention relates to a method and apparatus for making metallurgical tests. Although the invention is generally applicable, it is of particular application in the context of austenitic steels used in harsh environments, for example in the long pipes found in the pyrolysis section of petroleum cracking plants.

In a petroleum cracker, hydrocarbon molecules such as ethane and propane from natural gas, or heavier liquids such as naphtha and gas oil from petroleum are split into smaller molecules. This is often done to provide olefins such as ethylene that are useful in themselves, or may be used in polymerisation processes.

In the case of ethane and propane, the gas is heated to above about 800° C. at which point bonds within the molecule break, producing a range of smaller molecules. The desired products are then separated out. The same principle applies when cracking heavier substances, but since the molecules are much larger, a far greater range of smaller molecules is provided. Although such processes provide a smaller yield of olefins, many other useful by-products are produced.

In a typical ethane cracker plant, the cracking takes place in a pyrolysis section. Here, ethane is pumped through a maze of 4-6 inch diameter tubes located within a furnace. This is essentially a large firebox containing a large number of gas burners that are carefully arranged and directed to provide even heating of the tubes. As the ethane flows through the tubes it is heated up to about 800° C. and cracks. The ethane never comes into direct contact with the burner flames; if it were to do so it would ignite disastrously.

Ethane is pumped through the pyrolysis section at a very high rate. The residence time of any individual molecule is a few seconds or less in older plants and less than a one tenth of a second in more modern plants. It is important that the flow rate is kept this high in order to prevent the cracking process from running away. If it were to do so, the ethane would crack not into the desired products, but into methane or even carbon (coke) and hydrogen. A further measure that is taken to control the possibility of runaway is the mixing of steam with the ethane before it is fed to the furnaces. This has two beneficial effects. The first is to lower the temperature necessary for the cracking to take place and the second is to reduce the amount of coke formed and deposited on the inside of furnace tubes.

It will be appreciated that the combination of steam, hydrocarbons and very high temperatures poses a significant safety problem. As a result, great efforts are made to design plants that are safe, and once these have been constructed they must be maintained in a safe and useful condition. In particular, it is of the greatest importance that regular checks be made of critical components in the system. Having said that, modern petrochemical cracking plants are designed to produce vast quantities of product at a very high rate. The effect on the profitability of a plant of the necessary downtime when carrying out these vital safety checks is significant. There is therefore a great incentive for these checks to be carried out expeditiously.

As noted above, the pipes in the pyrolysis section carry a large quantity of highly reactive chemicals that must be kept at high temperature whilst being safely isolated from the heat source of the furnace. Although they are made of specialist steel, as noted above, they are operating in a very harsh environment involving high mechanical stress levels,.hash environment gases and gas composition variations which may, over time, lead to metallurgical problems. It is therefore important to check the integrity of the pipes, e.g. to spot excessive corrosion damage. In addition, it is,important to ensure that the burners are correctly aligned in order to ensure efficient operation of the furnace. Furthermore, incorrectly aligned burners may cause "hot spots" on the tubes that may result in local carburization and creep damage.

The steels used to form the pipes are usually austenitic. They rely on the chromium inherent in them to react with oxygen to form a dense layer of chromium oxide and also spinell oxides. This serves to protect the metal from further oxidation, thereby preventing the steel from corroding and in turn damaging the integrity of the structure.

The steel typically used in the furnace of an ethylene cracker comprises 25 per cent chromium, 35 per cent nickel, and 0.5 per cent carbon with the balance being iron. In the body of the steel, $Cr_{23}C_6$ precipitates out to form particles of high chromium content. The result of this is that most of the volume of the steel has about 20 per cent chromium content but with clusters of much higher chromium content located therein. The $Cr_{23}C_6$ clusters tend to dissolve over time and the chromium then migrates to the surface where it oxidises to form the protective surface oxide layer mentioned above —$Cr_3O_2$.

One problem that arises is that the harsh conditions in a pyrolysis furnace may cause a fast growing less protective oxide layer, oxide spallation and Cr evaporation. In some cases this type of corrosion will result in thinning of the metal and thus a weakening of the construction.

However, in an ethylene cracker the problem of possible faulty burner operation mentioned above is more significant. This is because faulty operation can over time lead to carburization and/or local creep damage and thus,possible tube failure. It is therefore highly desirable to be able to determine whether such faulty operation is occurring.

Viewed from a first aspect the invention provides a method of monitoring the condition and/or operation of a furnace comprising the step of measuring sub-surface chromium-depletion from a steel member.

The invention is particularly applicable to steel members in a pyrolysis furnace, but is useful in other harsh environments. In a pyrolysis furnace of a petroleum cracker the invention is particularly useful as part of the process of monitoring the state of the pipes through which the hydrocarbons flow, although it may be applied to other components.

The invention is based on the fact that the chromium flux towards the tube surface will, due to chromium evaporation, oxidation and oxide spallation, over time deplete an oxide sub-layer of chromium because the chromium diffusion in the alloy matrix is not very fast. The result of this is that, as well as a $Cr_3O_2$ layer being formed on the outside of the steel, a chromium-depleted layer is formed beneath the oxide layer. Whilst this depletion is not itself a particular problem, the inventors have recognized that, because of its relationship to the production of the oxide layer, the chromium-depleted layer provides useful data about the condition and operation of the furnace.

As excessive or rapid oxidation may result in pipe weakness, the ability to monitor the oxide layer in this way is useful in itself. Thus, viewed from another aspect the invention provides a method of determining the state of a surface oxide layer on a steel member by measuring the degree of chromium depletion in a sub-surface layer of the member.

Moreover, the growth rate of the oxide layer gives a useful indication of the condition of the pipe and the operating conditions of the reactor. A thick oxide layer, particularly one that is growing quickly and is therefore not tightly bonded to the remainder of the pipe, is not only an indication of pipe weakness but may also provide evidence of faulty burner operation leading to higher-than-desirable thermal load or greater temperature variation imposed on the tube in the region of the thick oxide formation. Thus, the chromium-depleted zone provides information about the oxide layer which in turn gives useful information about the operating conditions of the furnace. Accordingly, a preferred form of the invention uses the information determined about chromium depletion to detect pipe weakness and/or determine whether burner operation is satisfactory.

Although absolute measurements of chromium depletion are useful, in order to detect hot-spots caused by faulty burner operation, it is useful to compare chromium depletion levels from different areas of a steel member. Thus, preferably a number of measurements are taken at different points on a tube, e.g. along its length, and these are compared. An area where significantly higher than average depletion occurs is likely to correspond to a hot-spot.

Furthermore, it is preferred that the measurement(s) of the chromium depletion be repeated at intervals of time in order to provide information about the variation of the degree of chromium depletion with time.

The level of depletion and the depth of the chromium-depleted layer are related to the chromium loss rate from the surface and the growing rate of the oxide. This is so because the chromium flux towards the outer surface will generally decrease when the thickness of the oxide layer increases and the chromium diffusion from the inner alloy matrix will increase when the chromium level in the depleted zone decreases. Thus a steady state can become established where the chromium flux out of the depleted zone equals the chromium flux into the depleted zone. In this case the depleted zone thickness expresses the chromium loss rate and not the total amount of chromium lost in oxidation etc.

In some cases, for instance when there is an oxidation problem in the furnace, the oxidation is continuously fast and the amount of chromium lost to the surface is much higher than the (refill) chromium flux from the inner alloy matrix. In this case the level of chromium depletion is approximately proportional to the total amount of chromium lost over time (integrated rate). If all the chromium sticks to the surface as a thick fast growing oxide (without spallation and chromium evaporation) one could in this specific case say that the level of chromium depletion is proportional to the oxide thickness. Thus, at least under these conditions, the method of the invention preferably further comprises the step of determining the thickness of oxide on the steel member from the measured chromium depletion.

However the level of chromium depletion can also express something between the chromium loss rate and total chromium loss. Furthermore, the level of chromium depletion is strongly dependent of material quality.

Clearly, it is highly undesirable to have to make destructive tests such as cutting through the steel in order to examine its structure. Therefore, the invention preferably comprises the use of a non-destructive method of testing to measure chromium depletion.

Although other techniques could be used, it is preferred that the degree of chromium depletion is determined by taking advantage of the variation of the magnetic properties of steel as its chromium content decreases. Thus, preferably, a magnetic source of known strength is used to create a magnetic field in the surface region and then an estimate of the thickness of the chromium-depleted zone is determined from the resultant magnetic flux density at the surface of the member.

This measurement technique is believed to be independently inventive and so, viewed from another aspect, the invention provides a method of determining the thickness of a chromium-depleted zone of a surface region of a steel member comprising the steps of: using a magnetic source of known strength to create a magnetic field in the surface region and then determining an estimate of the thickness of the chromium depleted zone from the resultant magnetic flux density at the surface of the member.

This technique takes advantage of the fact that Austenitic steel is generally paramagnetic at room temperature (i.e. it has a magnetic permeability of just above unity). However, if the chromium content drops below about 13-18 per cent, then the Curie point rises to ambient temperature (in other words, the steel becomes ferromagnetic; it has a high magnetic permeability). The chromium-depleted layer has a chromium content of below 13-18 percent and is therefore ferromagnetic.

Thus, the magnetic properties of steel containing significant amounts of chromium are different from those containing a lesser amount. This has the result that, for a given magnetic field strength applied when the method of this aspect of invention is carried out, the flux density in such a region of the steel increases with increased chromium depletion. Therefore, by measuring the magnetic flux density, an indication of the amount of chromium depletion can be made and this in turn provides an estimate of the thickness of the chromium oxide layer.

By "measuring" it is not meant that a specific value of magnetic flux density in any standard unit is necessarily provided, although this could be done if desired. Rather, an output measurement which varies in a predictable manner in relation to changes in flux density is required. As noted above, in many instances all that is needed is to be able to compare measurements made at different places and/or times. However, if desired, the output may then be processed or suitably calibrated in order to provide an indication of the chromium depletion In order to calibrate the apparatus used, samples of steel with varying degrees of chromium depletion may be tested according to the method of this aspect of the invention. Subsequently, they may be cut up and the degree of chromium depletion determined using a scanning electron microscope. Field strength can then be correlated to chromium depletion for each type of steel tested. Since the magnetic properties of steel vary from one grade to another, it is desirable that for each grade that is to be tested by the method of the invention, samples of known layer thicknesses are tested.

It should be noted that the relationship between measured field strength and depletion-layer thickness is very non-linear. Indeed, for any test apparatus that is used, there will be a depletion-layer thickness that results in saturation.

For ease of measurement it is preferred that the magnetic source be arranged such that the flux density is measured at a position where the magnetic field lines are generally normal to the surface. It will be appreciated that as magnetic field lines are curved they cannot all be normal to the surface, but preferably the arrangement is such that the field lines in question are as near to normal as practicable.

In most cases the geometry is such that this objective can generally be achieved by using a magnet having its axis aligned at between 30 and 60 and more preferably between 40 and 50 degrees to the surface of the steel member. Most preferably, the axis is at substantially 45 degrees to the surface of the steel member.

Although an electromagnet may be used to generate the magnetic field of the invention, it is most convenient to use a permanent magnet. Preferably a fairly strong but small bar magnet is used. Typical dimensions will be between 0.5 and 20 mm, preferably around 10 mm in length and 2 to 5 mm, preferably around 3 mm in width. A useful field strength is between 300 and 400 milli-tesla, preferably around 350 milli-tesla. However, it will be appreciated that stronger magnets are needed where it is necessary to penetrate further into the steel.

Although any suitable means of measuring the magnetic flux may be applied, such as a search coil, it is most convenient to use a Hall effect device such as a commercially available Hall element. Such devices are generally around 3 mm square and are available as integrated units which are particularly convenient in the present application. Where the magnetic field lines are arranged to be generally perpendicular to the surface of the steel it follows that the sensing direction of the hall element should also be arranged to be normal to the surface. Thus, in the standard integrated unit this means that the larger base surface be applied or held proximate to the surface of the steel member.

Preferably the Hall element and magnet are very close together, if not touching. In the most preferred form of the invention the sensing direction of the Hall element is arranged at 45 degrees to the axis of the magnet.

In order to secure the components together it is preferred that a small housing be provided such that the entire apparatus needed to perform a sensing part of the invention forms a small and compact unit. Since in use the unit will generally be moved across the surface of the steel member it is preferred that a hard non-magnetic pad be provided under the Hall element to prevent damage caused by friction. This should preferably only be a millimetre or two in thickness to avoid reducing the sensitivity of the device.

A Hall element or other sensor will provide an output voltage which may then be converted into a suitable form to indicate the degree of chromium depletion. In the simplest case, it may be fed directly to a suitably calibrated voltmeter to provide a direct reading. With a more sophisticated device, the output signal from the probe may be fed to a computer, generally via an analogue-to-digital converter. A suitable program may be arranged to convert the input signal to a useful reading. This could perhaps be based upon first principles (i.e. a mathematical model), but it will be more straightforward to interpolate from a look-up table based upon experimental tests. As noted above, there will be a layer thickness where saturation occurs such that the output voltage from the Hall element reaches a maximum. Preferably means is provided to indicate when this occurs. It is, of course desirable to design the apparatus used such that saturation occurs at a depletion layer thickness that is greater than that likely to be found.

It will be appreciated from the foregoing that the invention also extends to a dedicated apparatus for performing the invention and therefore viewed from a further aspect the invention provides an apparatus for determining the thickness of a chromium depleted zone of a surface region of a steel member, the apparatus comprising a magnetic field source and a means for measuring the magnetic flux density, wherein the apparatus is arranged such that when it is placed proximate to a steel member the measuring means determines the magnetic flux density in the surface region of the steel resulting from the magnetic field source.

Preferably, the invention further provides means for providing an indication of the chromium depletion based upon the flux density.

Furthermore, the apparatus is preferably arranged to operate in accordance with one or more of the preferred forms of the method set forth above. In a particularly preferred form, the apparatus comprises a hall element having its axis arranged at substantially 45 degrees to the longitudinal axis of a bar magnet. Preferably these components are contained in a housing and furthermore it is particularly preferred that a protective pad be provided under the hall element. An output signal from the Hall element is preferably fed via an analogue-to-digital converter to a suitable computer as discussed above.

A preferred embodiment of the invention will now be described, with reference to the accompanying drawings, in which:

FIG. 3 is a generally schematic view illustrating the magnetic flux lines in a non-depleted steel surface;

FIG. 4 is a view corresponding to FIG. 3 in which the chromium has been depleted;

Figure 1:
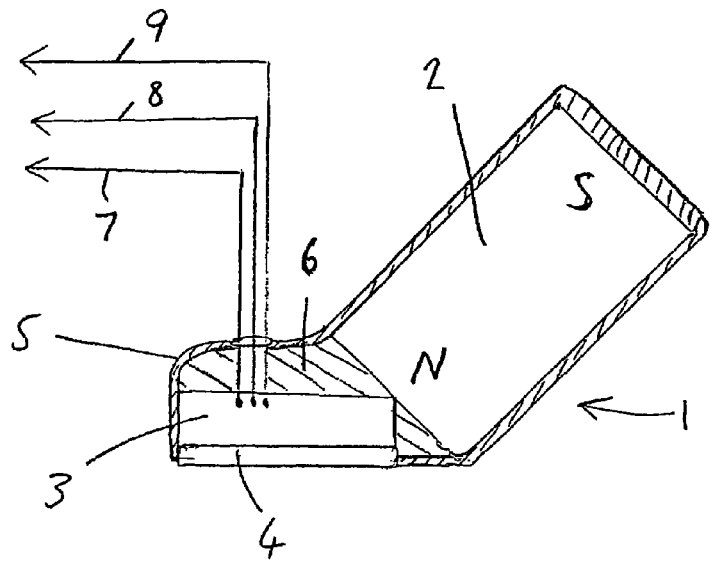
FIG. 1 is a partially sectional view of a probe according to the invention.

With reference first to FIG. 1, probe 1 comprises a bar magnet 2 of 10×3 mm in size and having a strength of 350 milli-teslas. It is located against a Hall element 3 with its axis at 45 degrees to the sensing axis of the Hall element. Hall element 3 is provided with a protective pad 4 at its base made of non-magnetic metal.

These components are all located within a plastic housing 5 and are interconnected by means of epoxy resin 6 which fills the void within the housing. Conductive leads 7, 8 and 9 extend through the epoxy and through an opening in the upper portion of the probe. Lead 9 provides a DC input to drive the Hall element, lead 8 is common and lead 7 provides a signal output from the Hall element. The Hall element is a standard commercially available integrated device. Leads 7, 8 and 9 will generally be provided within a flexible coiled cable such that the probe can be readily moved over a surface that is being tested.

Figure 2:
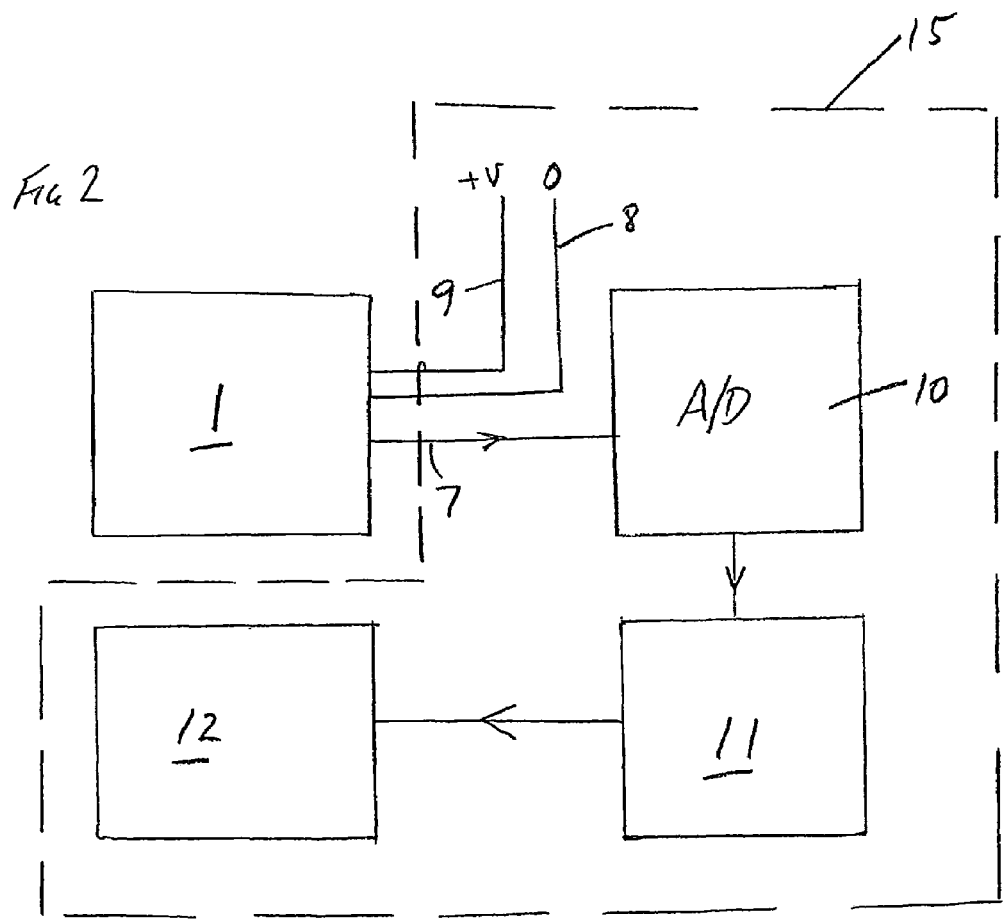
FIG. 2 is a schematic block diagram illustrating the interconnection of the probe and other components.

As may be seen from FIG. 2, the probe 1 is connected via signal lead 7 to an analogue to digital converter 10. Leads 8 and 9 are connected as previously mentioned. The digital output from converter 10 is then fed to a computer processor 11 in which software converts the signal into a value corresponding to the thickness of the chromium depletion layer of the steel member being tested. This is done by means of the results of empirical calibration tests whose results are stored in look-up tables. The processor may also be programmed to determine estimates of chromium oxide layer thickness. This is then displayed on a suitable display means 12.

As shown in the figure, components 10, 11 and 12 are conveniently provided together in a single portable integrated package 15 with the probe 1 being separate and freely moveable in relation to it. Alternatively, the analogue to digital converter could be provided integrally with, the probe and components 11 and 12 could be the respective parts of a standard personal computer.

FIG. 3 illustrates the probe 1 in position against a steel member 13 which does not have a depleted chromium layer. As may be seen, where the chromium is not depleted the magnetic field lines are significantly spaced apart as a result of the lower magnetic permeability of the steel. In contrast to this, FIG. 4 illustrates a depleted layer 14 near the surface of steel member 16 which has a much higher magnetic permeability. This results in the magnetic field lines being closer together in the same way as an iron core in an electromagnet.

It will be appreciated that by detecting the change in the magnetic flux density measured by the Hall probe an indication of the level of chromium depletion (which is proportional to depletion layer thickness) can be achieved. The voltage level on signal line 7 is predictably related (non-linearly) to the thickness of the depletion layer. Consequently, once the signal has been converted to digital form it may be processed in processor 11, for example by interpolating from a suitable experimentally-derived look-up table. The oxide layer thickness is in turn related to the thickness of the depletion layer and may also be determined in a similar manner.

Finally, a suitable output, such as the estimated chromium depletion layer thickness in microns and/or the raw output voltage from the probe, may be displayed on display unit 12.

In order to demonstrate the operation of the probes according to the invention, a series of simulation-based experiments have been carried out using ferromagnetic foils to simulate chromium-depleted layers.

Figure 5:
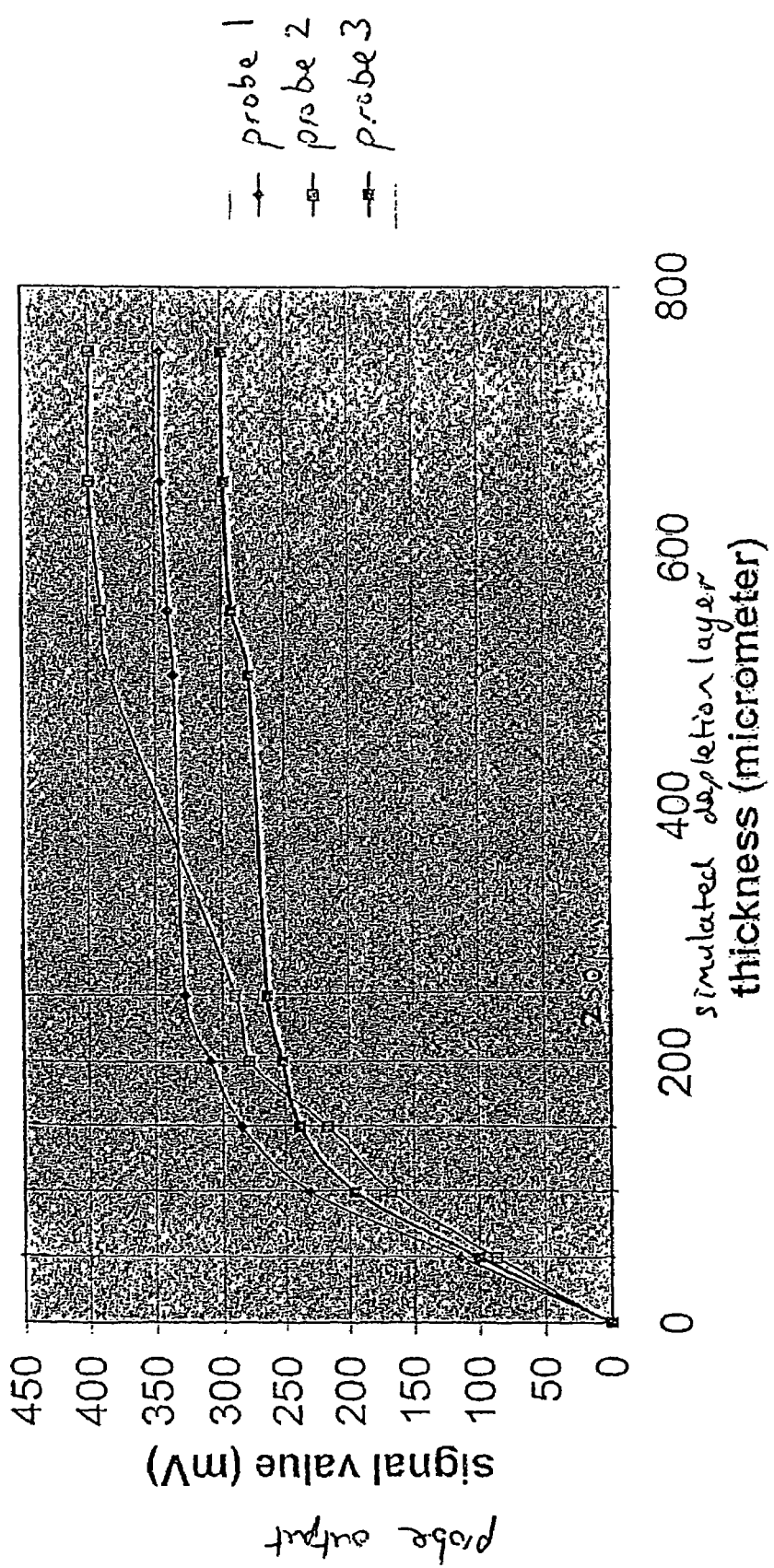
FIG. 5 is a graph illustrating the output voltage from three different probes according to the invention plotted against simulated depletion layer thickness.

Output voltage readings from three different probes (identified as probes 1-3) are shown in FIG. 5 as a function of a ferromagnetic foil thickness. Here the probes were placed directly against foils varying in thickness. As may be seen, there is a significant and clearly detectable variation in output voltage with thickness up to around 200 μm. Beyond this the variation becomes significantly less and above around 500 μm saturation occurs.

Figure 6:
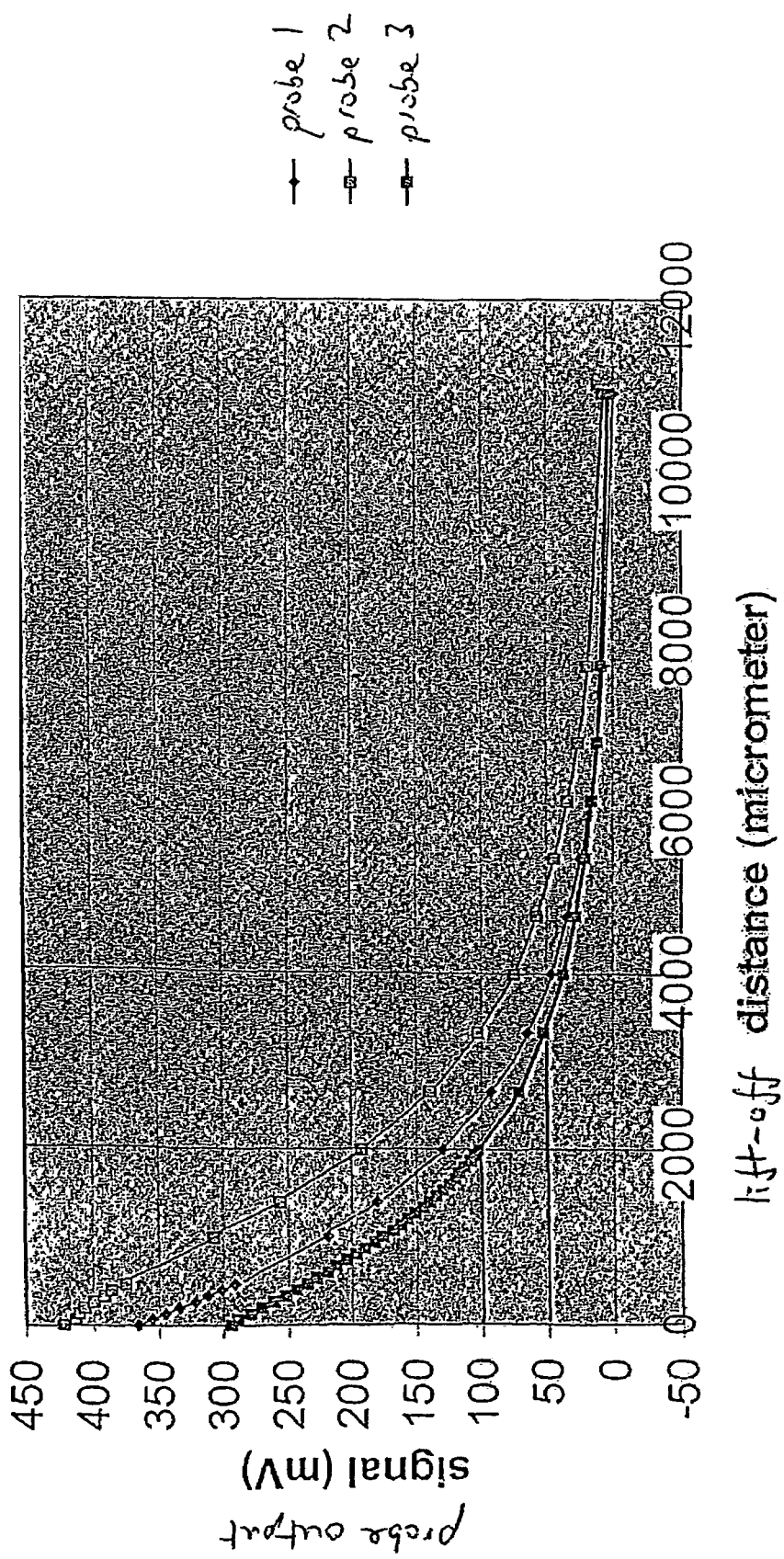
FIG. 6 is a graph illustrating the variation in output voltage from the same sensors as in FIG. 5 as the distance between the probes and the depletion layer is varied.

Since the ferromagnetic chromium-depleted layer is actually found below the surface of the steel, tests were also carried out to determine the effect of moving the probe away from the ferromagnetic foils. The influence from this so-called 'lift off' on the readings is shown in FIG. 6. Here the same three sensors were used to make measurements on a thick ferromagnetic surface. The distance between the base of the probe and the ferromagnetic material was varied and the output voltages recorded. It may be observed that as the lift-off increases beyond about 2000 μm, the output signal becomes significantly reduced. Nevertheless, it will be seen from FIGS. 5 and 6 that the probe is suitable for providing useful data from typical chromium-depleted layers which are located just below the outer oxide layer.

Figure 7:
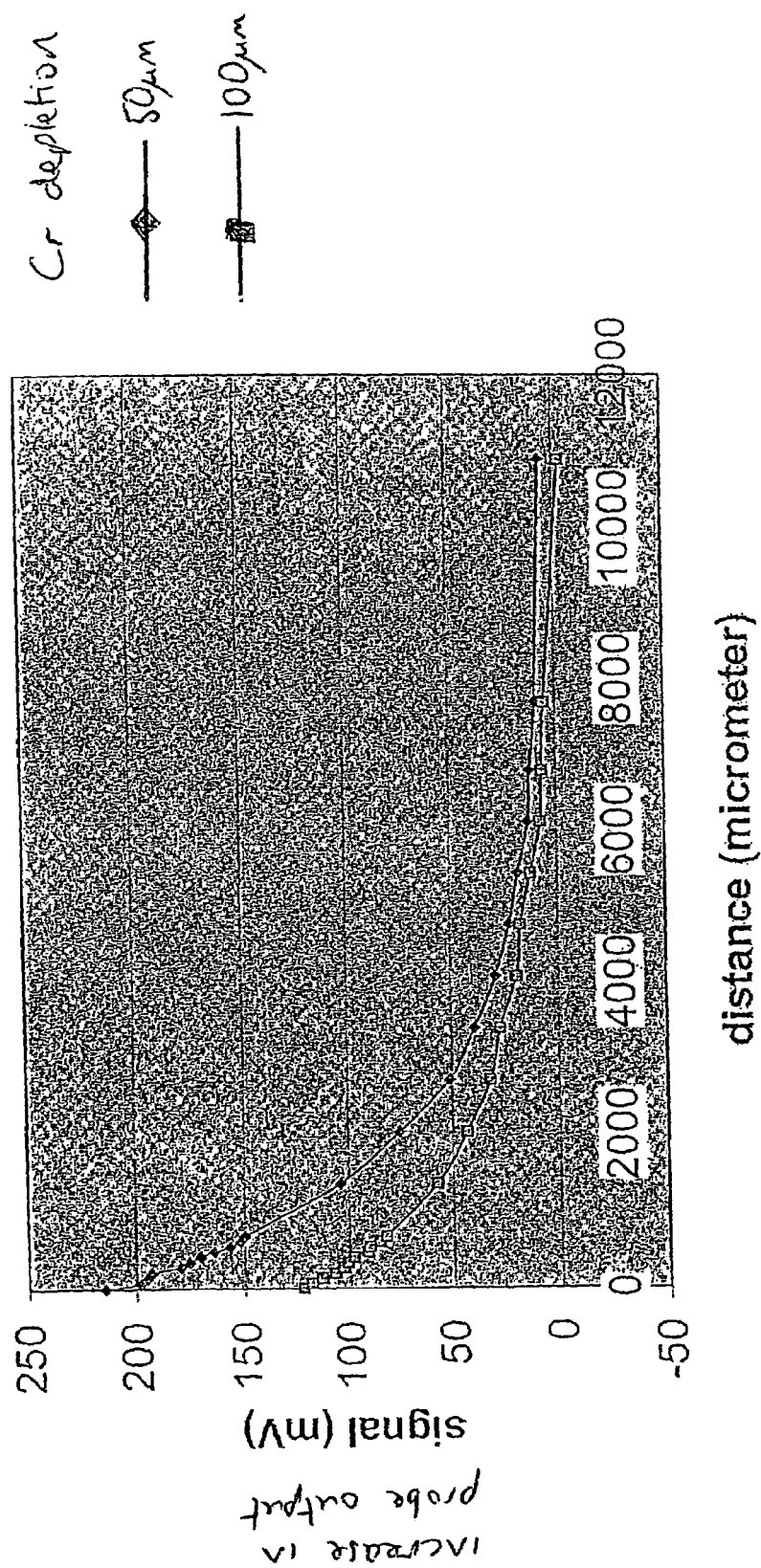
FIG. 7 is a graph illustrating the change in output voltage from a sensor according to the invention caused by the presence of a simulated layer of carburized steel.

In fact, at least in the context of a pipe in a pyrolysis furnace, it is undesirable for the probe to be affected by ferromagnetic layers deep below the surface because these may be caused by carburization of the inside surface of the pipe. A major reason for the actual geometric arrangement of the magnet and the Hall element shown in FIG. 1 is the desire to minimize the interference from a magnetic carburized area deeper into the material. FIG. 7 shows how the measured output voltages from a probe placed on simulated 50 μm and 100 μm thick depleted zones is influenced by a simulated carburized area. Ferromagnetic steel representing carburized steel was located at varying distances beneath foils representing a chromium-depleted layer. The indicated signal voltage is the increase caused by the presence of ferromagnetic steel. One can see that in the case of the 100 μm depleted layer, when the carburized area is located more than 2 mm underneath it the readings from the probe (which was 200 mV without the "carburized" steel present) is increased only moderately by about 50 mV (to 250 mV). Therefore, for any useful pipe thickness it can be assumed that carburization of the interior of the pipe should not cause significant inaccuracies in the output readings.

Figure 8:
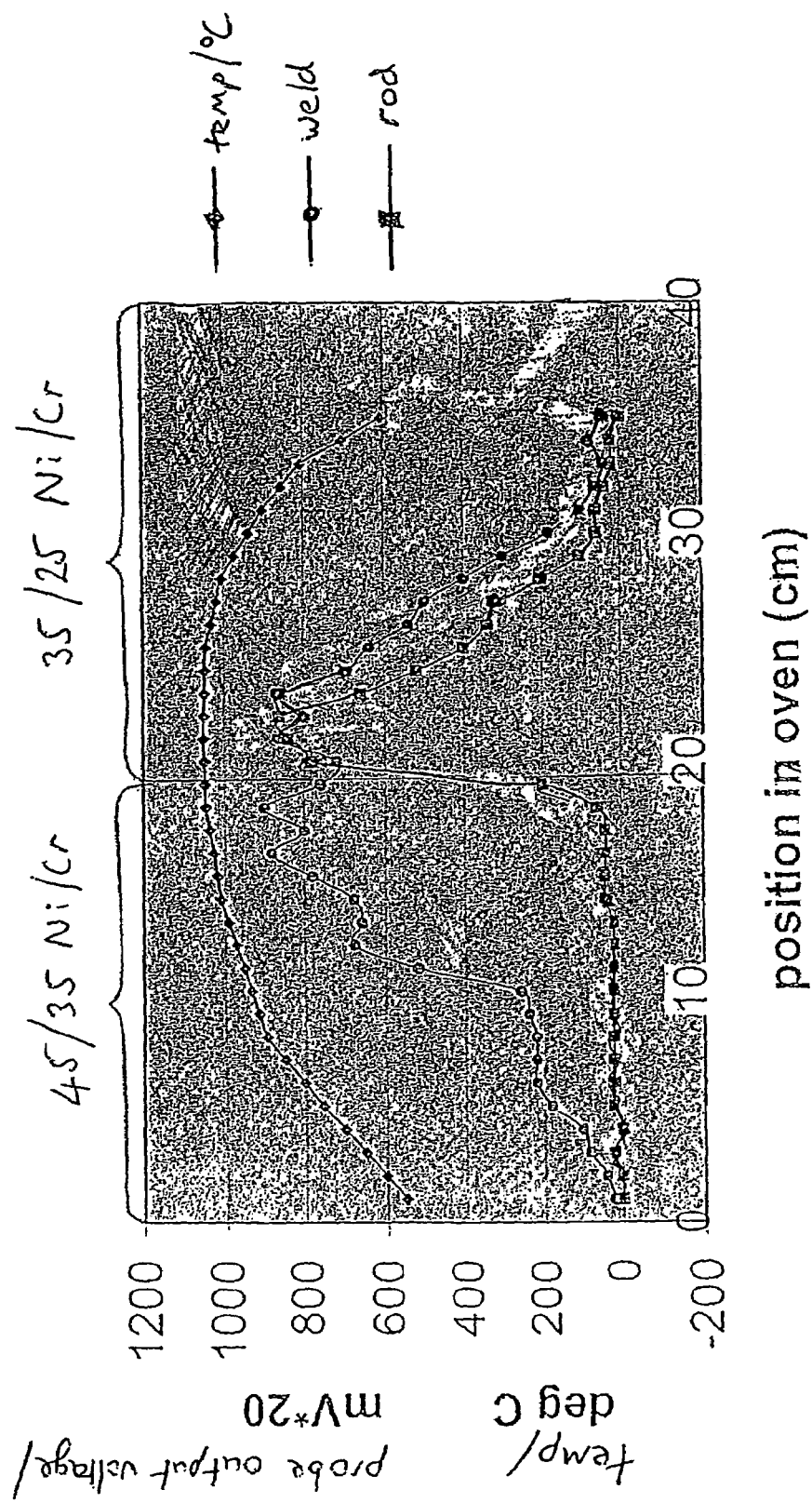
FIG. 8 is a graph comparing the output voltages produced by a probe according to the invention when applied to two different grades of steel that had been subjected to high temperatures.

Finally, FIG. 8 illustrates the result of an experiment where a probe according to the invention was used to test a steel rod that had been subjected to high temperatures.

In order to compare the output signals caused by different degrees of oxidation on different grades of steel, the rod was welded together from two halves made of different materials: 25/35 Cr/Ni and 35/45 Cr/Ni. It was exposed to cyclic oxidation for about 1000 hours in an oven having a temperature gradient of 600° C. to 1040° C.

The figure has one line to indicate the variation of temperature (degrees Celsius) with position in the oven. The other two lines indicate output voltages from a sensor placed at different positions firstly on a weld on the rod and secondly on the rod itself.

It may bee seen that the weld, which is symmetrically installed in the furnace, gives a reading proportional to the temperature in both halves of the furnace. The 25/35 Cr/Ni and 35/45 Cr/Ni materials also give readings proportional to the local thermal load. However, the large difference between 25/35 Cr/Ni and 35/45 Cr/Ni material is apparent. This indicates the difference in oxidation resistance between these two materials.

As discussed above, it would be necessary to calibrate the probe for each material type before the readings from different alloys could be compared. However where the probe is used to identify irregularities in the furnace operation (for example looking for "hot spots" caused by poor burner set-up) the relative probe readings obtained from the same material type and age could be used. For example, a series of measurements may be taken along the length of a particular pipe and/or at different places around its circumference.

If necessary, the movement of this probe over the surface of the steel member may also be measured in a known manner and this, in combination with oxide layer thickness data may be used to provide a map on display 12 showing the variation of the output voltage (or depletion layer thickness if calibrated) along the member.

The invention claimed is:

1. A method of monitoring the condition and/or operation of a furnace comprising measuring sub-surface chromium-depletion from a steel member wherein a magnetic source of known strength is used to create a magnetic field in the surface region of the steel member and an estimate of the thickness of the chromium-depleted zone is determined from the resultant magnetic flux density at the surface of the steel member, wherein the magnetic field is created in the surface region by a magnet having its axis at between 30 degrees and 60 degrees to the surface of the steel member.

2. A method as claimed in claim 1, wherein the steel member is a pipe within a pyrolysis furnace through which hydrocarbons flow.

3. A method as claimed in claim 1, further comprising the step of using the measurement of chromium depletion to estimate the state of a surface oxide layer.

4. A method as claimed in claim 1, further comprising the step of using the measurement of chromium depletion to determining whether burners in the furnace are operating satisfactorily.

5. A method of determining the thickness of a chromium-depleted zone of a surface region of a steel member comprising the steps of using a magnetic source of known strength to create a magnetic field in the surface region and then determining an estimate of the thickness of the chromium depleted zone from the resultant magnetic flux density at the surface of the member, wherein the magnetic field is created in the surface region by a magnet having its axis at between 30 degrees and 60 degrees to the surface of the steel member.

6. A method as claimed in claim 5, wherein the flux density is measured at a position where the magnetic field lines are generally normal to the surface.

7. A method as claimed in claim 5, wherein the axis of the magnet is at substantially 45 degrees to the surface of the member.

8. A method as claimed in claim 5, wherein the magnetic field is created by a permanent magnet.

9. A method as claimed in claim 5, wherein the magnetic flux density is determined by a Hall-effect probe located proximate the surface of the steel member.

10. A method as claimed in claim 9, wherein a hard non-magnetic pad is provided between the Hall-effect probe and the surface.

11. A method as claimed in claim 9, wherein the field detection axis of the Hall-effect probe is aligned at substantially 45 degrees to the north-south axis of the source of the magnetic field.

12. A method as claimed in claim 9, wherein an output signal from the Hall-effect probe is processed in order to provide a direct indication of the thickness of the chromium depleted zone and/or the thickness of an associated oxide layer.

13. A method as claimed in claim 5, further comprising the step of determining an estimate of the surface oxide layer thickness.

14. Apparatus for determining the thickness of a chromium depleted zone of a surface region of a steel member, the apparatus comprising a magnetic field source and a means for measuring magnetic flux density, the magnetic field source positioned at an angle of between 30 degrees and 60 degrees with respect to the means for measuring magnetic flux density, wherein the apparatus is arranged such that when the means for measuring magnetic flux density is placed proximate to a steel member the measuring means determines the magnetic flux density in the surface region of the steel resulting from the magnetic field source and measures the subsurface chromium-depletion from the steel member.

15. Apparatus as claimed in claim 14, further comprising means to process the output from the measuring means and to display the thickness of the chromium depleted zone and/or the thickness of an associated oxide layer.

16. Apparatus as claimed in claim 14, wherein the means for measuring magnetic flux density is a Hall element and the magnetic field source is a bar magnet.

17. Apparatus as claimed in claim 14, wherein the magnetic field source is positioned at an angle of about 45 degrees with respect to the means for measuring magnetic flux density.

* * * * *